(12) United States Patent
Akhoondi et al.

(10) Patent No.: US 10,687,693 B2
(45) Date of Patent: Jun. 23, 2020

(54) ENDOSCOPE WITH IMPROVED CLAMPING CONNECTION FOR EASY DISMANTLING

(71) Applicant: KARL STORZ SE & Co. KG, Tuttlingen (DE)

(72) Inventors: Maryam Akhoondi, Tuttlingen (DE); Hans Appenzeller, Tuttlingen (DE); Vitali Jerjomin, Laagri (EE); Igor Monakov, Laagri (EE); Mauno Poldmann, Laagri (EE)

(73) Assignee: Karl Storz SE & Co. KG, Tuttlingen (DE)

( * ) Notice: Subject to any disclaimer, the term of this patent is extended or adjusted under 35 U.S.C. 154(b) by 273 days.

(21) Appl. No.: 15/782,274

(22) Filed: Oct. 12, 2017

(65) Prior Publication Data
US 2018/0168435 A1    Jun. 21, 2018

(30) Foreign Application Priority Data

Dec. 15, 2016 (DE) .................... 10 2016 124 553

(51) Int. Cl.
*A61B 1/005* (2006.01)
*A61B 1/00* (2006.01)

(52) U.S. Cl.
CPC .......... *A61B 1/0052* (2013.01); *A61B 1/0008* (2013.01); *A61B 1/00039* (2013.01);
(Continued)

(58) Field of Classification Search
CPC . A61B 1/0052; A61B 1/00039; A61B 1/0008; A61B 1/00098; A61B 1/0057;
(Continued)

(56) References Cited

U.S. PATENT DOCUMENTS 4,257,420 A * 3/1981 Terayama .............. A61B 17/12
                                                        600/104
5,423,835 A * 6/1995 Green et al. ....... A61B 17/1285
                                                        227/901
(Continued)

FOREIGN PATENT DOCUMENTS

DE    102012009332 A1    11/2013
EP          1112019 A1     7/2001

OTHER PUBLICATIONS

German Search Report Application No. 10 2016 124 553.4 Completed Date: Nov. 20, 2017; dated Nov. 23, 2017 16 Pages.

*Primary Examiner* — John P Leubecker
*Assistant Examiner* — Minqiao Huang
(74) *Attorney, Agent, or Firm* — Whitmyer IP Group LLC

(57) ABSTRACT

The invention relates to an endoscope with a shaft, in which at least one working channel is arranged, and with an endoscope head arranged at the distal end of the shaft, wherein a deflection lever is arranged in the endoscope head and is adjustable between a non-deflected starting position and a deflected working position relative to the shaft, and wherein the deflection lever is adjustable via a Bowden wire, the proximal end of which is mounted via a collet on a control handle arranged at the proximal end of the shaft, wherein the collet fixing the proximal end of the Bowden wire is arranged on a slide that is movable proximally out of a housing of the control handle, which slide is coupled to the control handle via a rod. In order to create an endoscope which, having a simple structure, can be easily dismantled, in particular for cleaning purposes, and reassembled, the invention proposes that the slide can be coupled to the rod via a clamping connection.

4 Claims, 4 Drawing Sheets

(52) U.S. Cl.
CPC ........ *A61B 1/0057* (2013.01); *A61B 1/00066* (2013.01); *A61B 1/00098* (2013.01); *A61B 1/00121* (2013.01); *A61B 1/00128* (2013.01)

(58) Field of Classification Search
CPC ............ A61B 1/00066; A61B 1/00121; A61B 1/00128
See application file for complete search history.

(56) References Cited

U.S. PATENT DOCUMENTS

| | | | | |
|---|---|---|---|---|
| 5,690,652 | A * | 11/1997 | Wurster | A61B 17/0469 |
| | | | | 606/139 |
| 5,730,152 | A * | 3/1998 | Esser | A61G 13/12 |
| | | | | 128/845 |
| 6,699,183 | B1 * | 3/2004 | Wimmer | F16C 1/14 |
| | | | | 600/104 |
| 2002/0042606 | A1 * | 4/2002 | Castaneda | A61B 17/3417 |
| | | | | 606/1 |
| 2012/0253330 | A1 * | 10/2012 | Ries | A61B 17/162 |
| | | | | 606/1 |
| 2016/0206383 | A1 * | 7/2016 | Leong | A61B 34/20 |
| 2018/0249894 | A1 * | 9/2018 | Kolberg | A61B 1/00137 |

* cited by examiner

ENDOSCOPE WITH IMPROVED CLAMPING CONNECTION FOR EASY DISMANTLING

TECHNICAL FIELD

The invention relates to an endoscope with a shaft, in which at least one working channel is arranged, and with an endoscope head arranged at the distal end of the shaft, wherein a deflection lever is arranged in the endoscope head and is adjustable between a non-deflected starting position and a deflected working position relative to the shaft, and wherein the deflection lever is adjustable via a Bowden wire, the proximal end of which is mounted via a collet on a control handle arranged at the proximal end of the shaft, wherein the collet fixing the proximal end of the Bowden wire is arranged on a slide that is movable proximally out of a housing of the control handle, which slide is coupled to the control handle via a rod.

BACKGROUND

Endoscopes of this kind, for example duodenoscopes, with a lens system usually arranged laterally at the endoscope head have a deflection mechanism known as an Albarran lever, by which the probes or other medical instruments inserted through the at least one working channel into the endoscope are deflected laterally from the endoscope head and moved in the viewing angle of the lens system.

An endoscope of the type in question is known, for example, from EP 1 112 019 B1. Although this known endoscope has indeed proven itself in practice, it has the disadvantage that, in order to clean the at least one working channel and guide the Bowden wire, parts of the endoscope have to be dismantled by means of tools, for example screwdrivers, which procedure is time-consuming and, on account of the small component parts, also complicated.

SUMMARY

Proceeding from this, the object of the invention is to create an endoscope of the type mentioned at the outset which, having a simple structure, can be easily dismantled, in particular for cleaning purposes, and reassembled.

This object is achieved, according to the invention, by the fact that the slide can be coupled to the rod via a clamping connection.

Since the coupling between the rod, which serves to move the slide, and the slide itself is designed as a screwless clamping connection, it is easily possible to remove the slide for cleaning purposes from the housing of the control handle and reattach it after cleaning. The design as a clamping connection even permits dismantling and reattachment with just one hand.

According to a preferred embodiment for forming this clamping connection, the invention proposes that a longitudinal slit is formed in the rod and extends as far as that end of the rod couplable to the slide, and that a latching element that can be pushed into the longitudinal slit is formed on the slide. By means of the longitudinal slit formed in the rod, the rod can be bent resiliently apart in order to receive the latching element arranged on the slide. The restoring force of the two spring arms of the rod that are formed by the longitudinal slit then fixes and clamps the latching element of the slide pushed into the longitudinal slit.

In order to improve the clamping and fixing of the latching element of the slide in the longitudinal slit of the rod, it is proposed, in a practical embodiment of the invention, that a latching recess for receiving the latching element of the slide is formed in the longitudinal slit of the rod.

In order to form the latching element of the slide and to form the latching recess of the longitudinal slit, it is proposed according to the invention that the latching element on the slide is designed as a pin with a cross section in the shape of a mushroom and with a stem protruding at right angles from the slide, and with a head formed at the free end of the stem and exceeding the diameter of the stem, and that the latching recess of the longitudinal slit is designed as a recess adapted to a stem of the mushroom-shaped pin. The configuration of the latching element of the slide in the shape of a mushroom ensures that the rod cannot simply be pulled away from the latching element transversely with respect to the direction of the longitudinal slit.

According to an alternative embodiment of the invention, it is proposed that the endoscope head can be coupled to the distal end of the shaft via a clamping connection.

Since the coupling between the endoscope head and the distal end of the shaft is designed as a screwless clamping connection, it is easily possible to separate the endoscope head for cleaning purposes from the shaft and reattach it after cleaning. The design as a clamping connection even permits dismantling and reattachment with just one hand.

According to a preferred embodiment for forming this clamping connection, the invention proposes that a clamping slit is formed in the proximal end of the endoscope head, and that a latching element that is insertable into the clamping slit of the endoscope head is formed at the distal end of the shaft.

According to a preferred embodiment of the invention, the latching element at the distal end of the shaft is designed as a latching lug that continues the shaft in the distal direction.

The design of the connection of the endoscope head to the shaft as purely a clamping connection is particularly advantageous in the case where the module forming the endoscope head is produced as a disposable article made of a plastics material.

Finally, the invention proposes both that the endoscope head can be coupled to the distal end of the shaft via a clamping connection and also that the slide can be coupled to the rod via a clamping connection.

The structural design of these two connections as clamping connections permits simple dismantling and reattachment of the component parts and is particularly advantageous in respect of rapid, easier and complete cleaning of the endoscope.

BRIEF DESCRIPTION OF THE DRAWINGS

Further features and advantages of the invention will become clear from the accompanying drawings in which an illustrative embodiment of an endoscope according to the invention is shown purely by way of example, without limiting the invention to this illustrative embodiment. In the drawings.

DETAILED DESCRIPTION

Figure 1:
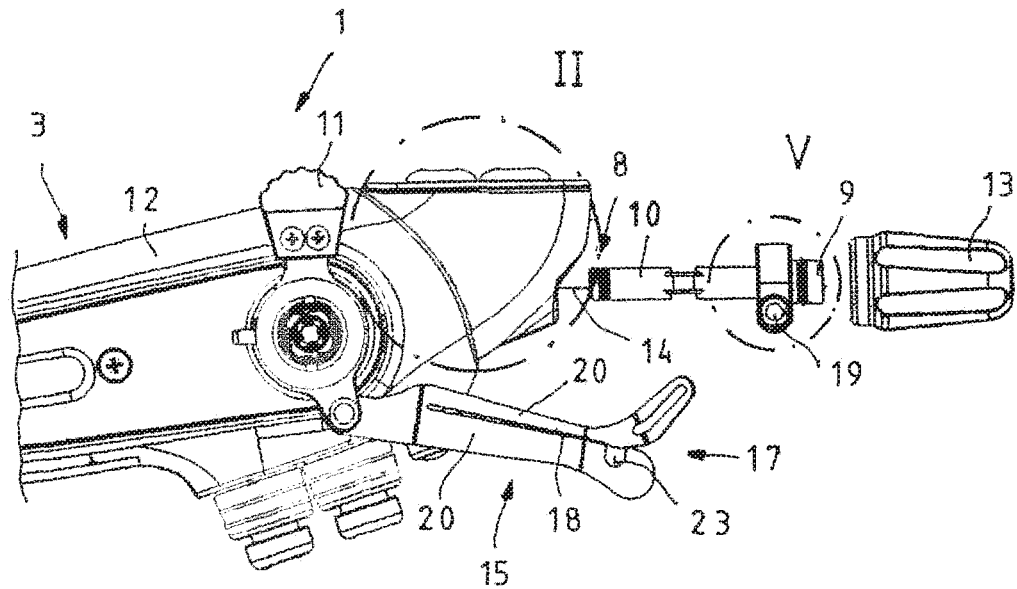
FIG. 1 shows a side view of a detail of a control handle of an endoscope according to the invention, with the collet depicted in the dismantled state.
Figure 3:
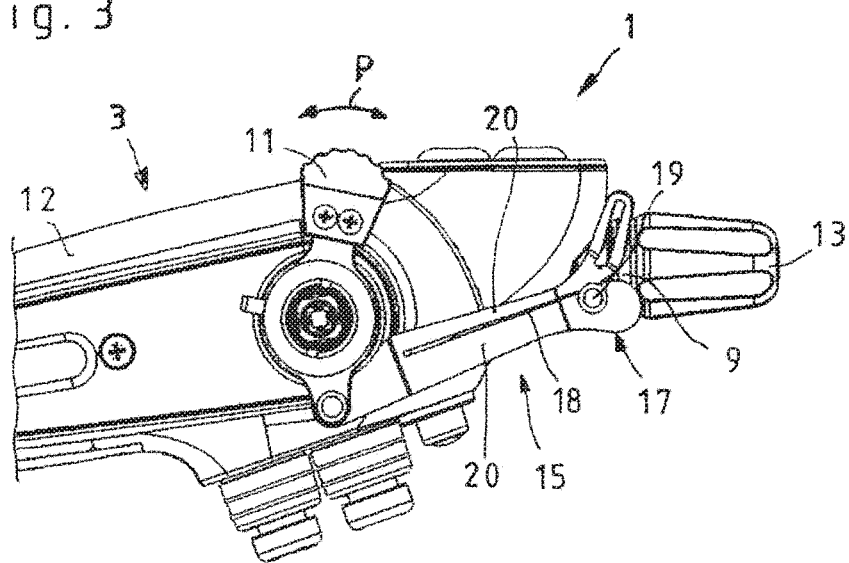
FIG. 3 shows a view according to FIG. 1, with the collet depicted in an assembled starting position.
Figure 4:
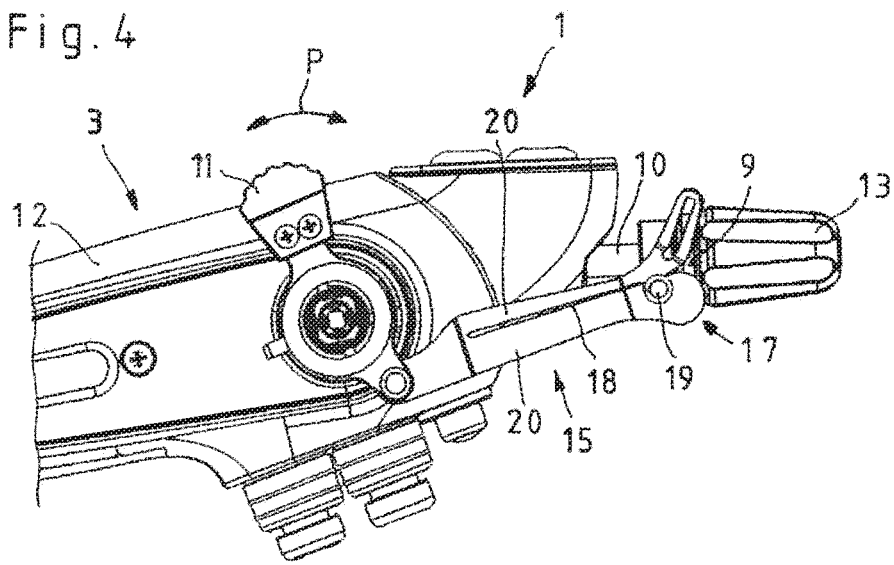
FIG. 4 shows a view according to FIG. 3, with the collet depicted in a deflected working position.
Figure 6:
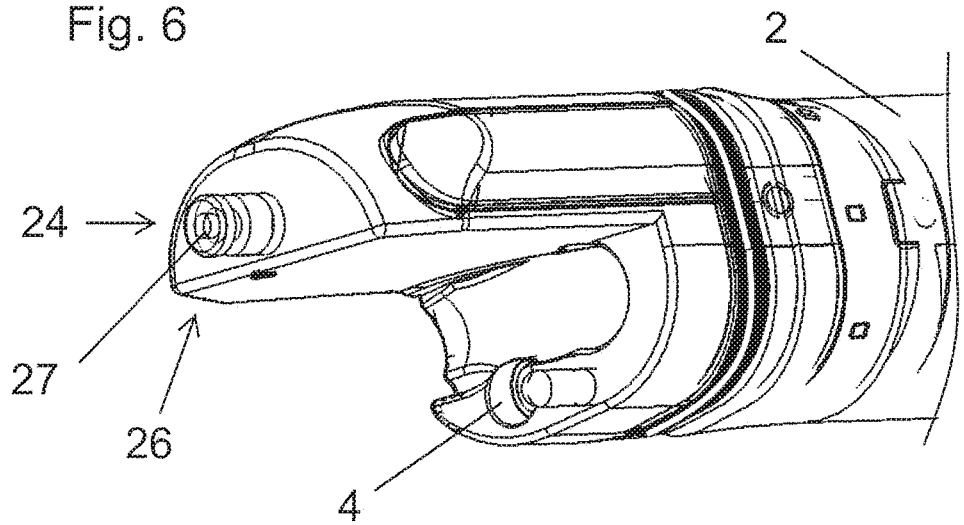
FIG. 6 shows a perspective view of the distal end of the shaft with the endoscope head dismantled.
Figure 6:
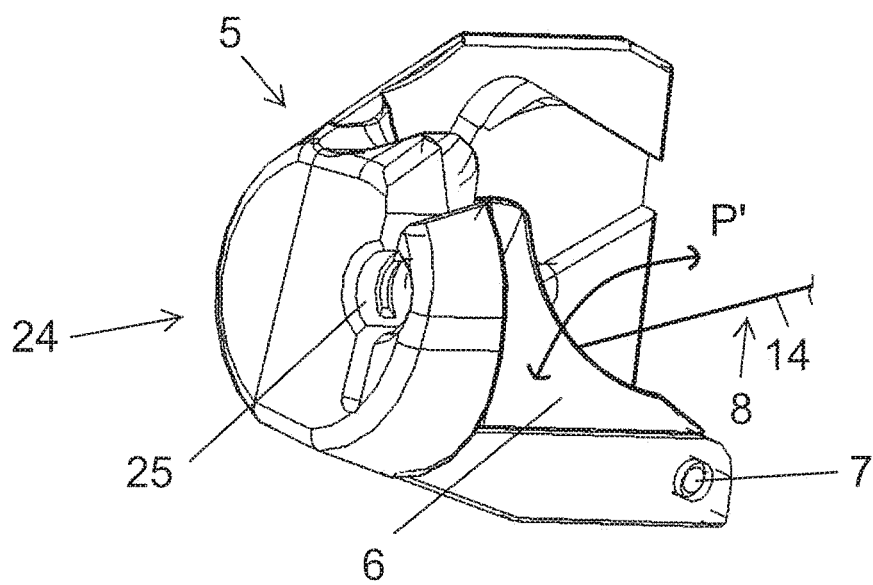

FIGS. 1, 3 and 4 show the proximal end of an endoscope 1 designed for example as a duodenoscope, with a control handle 3 forming the proximal end of a flexible shaft 2 (see FIG. 6).

Referring to FIG. 6, at least one working channel 4 is formed in the interior of the shaft 2 and extends in the longitudinal direction of the shaft 2, and medical instruments, for example probes or catheters, can be fed to the examination site via said working channel 4.

Figure 7:
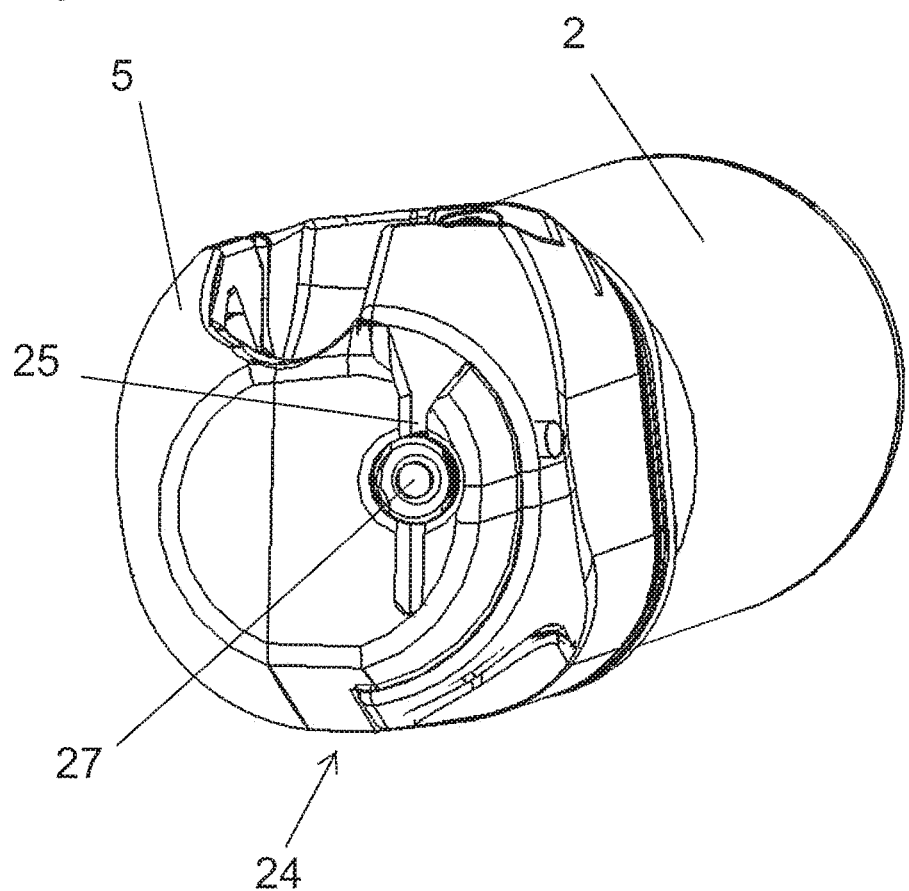
FIG. 7 shows a view rotated through 90° in relation to the view according to FIG. 6, depicting the distal end of the shaft with the assembled endoscope head.

Referring to FIGS. 6 and 7, at the distal end of the flexible shaft 2 is an endoscope head 5 which, designed as an exchangeable module, can be secured to the distal end of the shaft 2.

To ensure that the medical instruments inserted through the at least one working channel 4 into the endoscope 1 can be deflected laterally from the shaft 2 and introduced into laterally branching channels of the examination site, for example bile ducts, an adjustable deflection lever 6 is arranged in the endoscope head 5 and is adjustable between the non-deflected starting position, shown in FIG. 6, and the deflected working position relative to the shaft 2, shown in FIG. 7, wherein the deflection lever 6 in the embodiment shown is pivotable about a pivot axis 7 arranged transversely with respect to the longitudinal direction of the endoscope head 5. This deflection lever 6, also known as an Albarran lever, is adjusted via a Bowden wire 8 guided in the shaft 2.

The control handle 3 shown in FIGS. 1, 3 and 4, and forming the proximal end of the endoscope 1, has a control mechanism (not shown) via which the endoscope head 5 can be angled upward and downward and also to the right and to the left with respect to the shaft 2.

The proximal end of the Bowden wire 8 mounted distally on the deflection lever 6 is mounted in a collet 9 on the control handle 3. The collet 9 is in turn mounted on a slide 10 which, by way of a clamping lever 11 mounted on the control handle 3, is mounted displaceably in a housing 12 of the control handle 3 in such a way that the collet 9 protrudes proximally from the housing 12 of the control handle 3 in the working position, in which the Bowden wire 8 is tensioned and the deflection lever 6 is deflected.

The Bowden wire 8 is fixed in the collet 9 via a clamping nut 13 that can be screwed proximally onto the collet 9. To start with, the Bowden wire 8 is pushed into the shaft 2, from the direction of the distal end of the endoscope 1, until a wire pull 14 of the Bowden wire 8 emerges again proximally from the collet 9 mounted in the control handle 3. Thereafter, the clamping nut 13 is screwed onto the collet 9, as a result of which the proximal end of the collet 9 is compressed radially inward and the wire pull 14 of the Bowden wire 8 is thus securely fixed in the collet 9.

FIGS. 1, 3 and 4 show the control handle 3 without the control mechanism needed for setting the endoscope head 5 at an angle. The clamping lever 11 mounted rotatably on the control handle 3 is connected by a rod 15 to the slide 10 of the collet 9 mounted with a guiding action in a bore 16 (FIG. 2) in the housing 12 of the control handle 3, wherein the rod 15 is mounted eccentrically on the clamping lever 11, as can be seen from the figures.

FIG. 3 shows the collet 9 in the starting position, in which the Bowden wire 8 is not tensioned and the deflection lever 6 in the endoscope head 5 is located in the non-deflected position shown in FIG. 6. In this starting position, the clamping nut 13 screwed onto the collet 9 bears proximally almost flush on the housing 12 of the control handle 3.

When the clamping lever 11 of the control handle 3 is rotated in the direction of the arrow P, the rod 15 mounted eccentrically at one end on the clamping lever 11 and at the other end on the slide 10 moves the slide 10, mounted in the bore 16, along with the collet 9, mounted on the slide 10, in the proximal direction, such that the collet 9 emerges proximally from the housing of the control handle 3, as is shown in FIG. 4. In this clamping position, the clamping nut 13 is clearly spaced apart from the housing 12 of the control handle 3 in the proximal direction.

This proximally directed displacement of the proximal end of the wire pull 14 of the Bowden wire 8, fixed in the collet 9, has the effect that, at the distal end of the Bowden wire 8, the deflection lever 6 is pivoted about the pivot axis 7 to the deflected working position with respect to the shaft 2, as is shown in FIG. 7 by the arrow P'.

Figure 2:
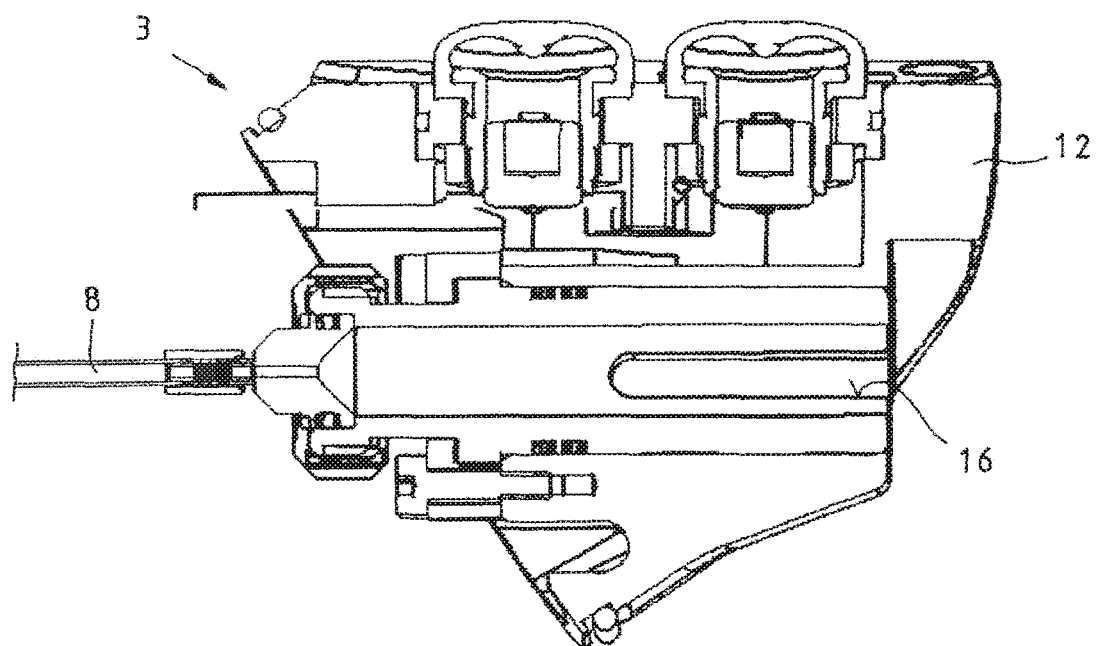
FIG. 2 shows an enlarged longitudinal section through the detail II according to FIG. 1.

To ensure that all the channels within the endoscope 1, for example the at least one working channel 4 and the bore 16 shown in FIG. 2 for receiving and guiding the slide 10, can be thoroughly cleaned after use, the endoscope 1 has to be partially dismantled into its individual parts.

In the depicted embodiment of the endoscope 1, the removal of the slide 10 from the housing 12 of the control handle 3 is made easier by the fact that the slide 10 can be coupled to the rod 15 via a screwless clamping connection 17. It is thus possible to separate the rod 15 from the slide 10 without the aid of a tool, in order to be able to pull the slide 10 out of the bore 16.

To form the clamping connection 17, a longitudinal slit 18 is formed in the rod 15 and extends as far as that end of the rod 15 couplable to the slide 10, and a latching element 19 that can be pushed into the longitudinal slit 18 is formed on the slide 10. By means of the longitudinal slit 18 formed in the rod 15, the rod 15 can be bent resiliently apart in order to receive the latching element 19 arranged on the slide 10. The restoring force of the two spring arms 20 of the rod 15 that are formed by the longitudinal slit 18 then fixes and clamps the latching element 19 of the slide 10, pushed into the longitudinal slit 18, between the two spring arms 20.

Figure 5:
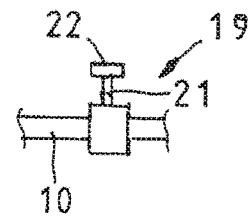
FIG. 5 shows an enlarged schematic side view of the detail V according to FIG. 1.

As can be seen from the side view according to FIG. 5, the latching element 19 on the slide 10 is designed as a pin with a cross section in the shape of a mushroom and with a stem 21 protruding at right angles from the slide 10, and with a head 22 formed at the free end of the stem 21 and exceeding the diameter of the stem 21.

In order to improve the clamping and fixing of the latching element 19 of the slide 10 between the spring arms 20 of the longitudinal slit 17 of the rod 15, a substantially circular recess 23 is formed in the longitudinal slit 17 and serves as a latching recess for receiving the latching element 19 of the slide 10.

Since the coupling between the rod 15, which serves to move the slide 10, and the slide 10 itself is designed as a screwless clamping connection 17, it is easily possible to remove the slide 10 for cleaning purposes from the housing 12 of the control handle 3 and reattach it after cleaning. The design as a clamping connection 17 even permits dismantling and reattachment with just one hand.

As can be seen from FIGS. 6 and 7, the endoscope head 5 is coupled to the distal end of the shaft 2 by a clamping connection 24.

Since the coupling between the endoscope head 5 and the distal end of the shaft 2 is designed as a screwless clamping connection 24, it is easily possible to separate the endoscope head 5 for cleaning purposes from the shaft 2 and reattach it after cleaning. The design as a clamping connection 24 even permits dismantling and reattachment with just one hand.

In order to form the clamping connection 24, a clamping slit 25 is formed in the proximal end of the endoscope head 5, and a latching element 26 that is insertable into the clamping slit 25 of the endoscope head 5 is formed at the distal end of the shaft 2. In the embodiment shown, the latching element 26 at the distal end of the shaft 2 is designed as a latching lug 27 that continues the shaft 2 in the distal direction.

The design of the connection of the endoscope head 5 to the shaft 2 as purely a clamping connection 24 is particularly advantageous in the case where the module forming the endoscope head 5 is produced as a disposable article made of a plastics material.

Although the proximal connection of the rod 15 to the slide 10 is a clamping connection 17 and the distal connection of the shaft 2 to the endoscope head 5 is also a clamping connection 24, in the embodiment of the endoscope 1 described above, it is of course also possible for just one of the two described connections to be designed as a clamping connection 17 or 24.

An endoscope 1 designed in the manner described above is distinguished by the fact that, having a simple structure, it can be easily dismantled, in particular for cleaning purposes, and reassembled.

LIST OF REFERENCE SIGNS 1 endoscope
2 shaft
3 control handle
4 working channel
5 endoscope head
6 deflection lever/Albarran lever
7 pivot axis
8 Bowden wire
9 collet
10 slide
11 clamping lever
12 housing
13 clamping nut
14 wire pull
15 rod
16 bore
17 clamping connection (slide—rod)
18 longitudinal slit
19 latching element
20 spring arm
21 stem
22 head
23 recess
24 clamping connection (endoscope head—shaft)
25 clamping slit
26 latching element
27 latching lug
P arrow
P' arrow

What is claimed is:

1. An endoscope, comprising:
a shaft, in which at least one working channel is arranged; and
an endoscope head arranged at a distal end of the shaft;
wherein a deflection lever is arranged in the endoscope head and is adjustable between a non-deflected starting position and a deflected working position relative to the shaft;
wherein the deflection lever is adjustable via a Bowden wire, a proximal end of which is mounted via a collet on a control handle arranged at a proximal end of the shaft;
wherein the collet fixing the proximal end of the Bowden wire is arranged on a slide that is movable proximally out of a housing of the control handle, which slide is coupled to the control handle via a rod, wherein the slide is coupled to the rod via a clamping connection; and
wherein the clamping connection is formed by a longitudinal slit formed in the rod and a latching element formed on the slide, wherein the longitudinal slit extends as far as an end of the rod couplable to the slide, and wherein the latching element is pushed into the longitudinal slit.

2. The endoscope according to claim 1, wherein a latching recess for receiving the latching element of the slide is formed in the longitudinal slit of the rod.

3. The endoscope according to claim 2, wherein the latching element on the slide is designed as a pin with a cross section in a shape of a mushroom and with a stem protruding at right angles from the slide, and with a head formed at a free end of the stem and exceeding a diameter of the stem.

4. The endoscope according to claim 3, wherein the latching recess of the longitudinal slit is designed as a recess adapted to a stem of the mushroom-shaped pin.

* * * * *